(12) United States Patent
Lauer et al.

(10) Patent No.: US 9,925,324 B2
(45) Date of Patent: Mar. 27, 2018

(54) RECEPTION MEANS FOR RECEIVING MEDICAL FLUIDS, AS WELL AS EXTERNAL FUNCTIONAL MEANS AND MEDICAL TREATMENT APPARATUS

(75) Inventors: Martin Lauer, St. Wendel (DE); Goetz Guenther, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1330 days.

(21) Appl. No.: 12/766,394

(22) Filed: Apr. 23, 2010

(65) Prior Publication Data

US 2010/0294398 A1 Nov. 25, 2010

Related U.S. Application Data

(60) Provisional application No. 61/185,607, filed on Jun. 10, 2009.

(30) Foreign Application Priority Data

Apr. 23, 2009 (DE) .......................... 10 2009 018 664
Jun. 10, 2009 (DE) .......................... 10 2009 024 466

(51) Int. Cl.
*A61M 1/14* (2006.01)
*A61M 1/36* (2006.01)

(52) U.S. Cl.
CPC ....... *A61M 1/3627* (2013.01); *A61M 2205/12* (2013.01); *A61M 2206/10* (2013.01)

(58) Field of Classification Search
CPC .............................. A61M 1/36; A61M 1/3621
See application file for complete search history.

(56) References Cited

U.S. PATENT DOCUMENTS

| | | | |
|---|---|---|---|
| 6,013,060 A | 1/2000 | Woodard | |
| 6,743,201 B1 | 6/2004 | Donig et al. | |
| 7,279,031 B1 | 10/2007 | Wright | |
| 7,279,903 B2 | 10/2007 | Quackenbush et al. | |
| 2004/0019313 A1* | 1/2004 | Childers | A61M 1/1696 604/5.01 |
| 2005/0230292 A1* | 10/2005 | Beden | A61M 1/1037 210/85 |

(Continued)

FOREIGN PATENT DOCUMENTS

DE 102 24 750 A1 12/2003
DE 10 2009 012 632.5 A1 9/2010

(Continued)

OTHER PUBLICATIONS

Evert, Alfred. "Physics and Philosophy". Books on Demand: 2008. p. 53. See attached.*

(Continued)

*Primary Examiner* — Tatyana Zalukaeva
*Assistant Examiner* — Sara Sass
(74) *Attorney, Agent, or Firm* — Fish & Richardson P.C.

(57) ABSTRACT

The present invention relates to a reception means for receiving fluids, which comprises a fluid surge redirection element comprising at least one flow-conditioning body that is adapted and intended to divide the fluid surge of the inflowing fluid into at least two partial fluid surges. It further relates to an external functional means as well as a treatment apparatus comprising a reception means in accordance with the invention.

24 Claims, 5 Drawing Sheets

(56) References Cited

U.S. PATENT DOCUMENTS

| | | | |
|---|---|---|---|
| 2006/0009727 A1* | 1/2006 | O'Mahony et al. | 604/4.01 |
| 2008/0097274 A1* | 4/2008 | Neri et al. | 604/6.15 |
| 2009/0084718 A1 | 4/2009 | Prisco et al. | |
| 2009/0084719 A1 | 4/2009 | Childers et al. | |
| 2009/0084721 A1* | 4/2009 | Yardimci et al. | 210/188 |
| 2009/0127288 A1 | 5/2009 | Keller | |
| 2010/0269702 A1* | 10/2010 | Brueckner | A61M 1/3627 96/212 |
| 2012/0095402 A1* | 4/2012 | Lande | 604/151 |
| 2012/0152118 A1* | 6/2012 | Weaver | A61M 1/3627 95/157 |

FOREIGN PATENT DOCUMENTS

| | | |
|---|---|---|
| DE | 10 2009 018 664.8 A1 | 10/2010 |
| DE | 10 2009 024 468.9 A1 | 12/2010 |
| DE | 10 2009 024 465.4 A1 | 1/2011 |
| JP | Y 1989012833 Y2 | 1/1989 |
| JP | H11-347115 A | 12/1999 |
| JP | H03099689 | 4/2004 |
| JP | 2006-512138 A | 4/2006 |
| JP | 2008544840 | 12/2008 |
| WO | 2004/060449 A2 | 7/2004 |
| WO | 2007/000066 A1 | 1/2007 |

OTHER PUBLICATIONS

Bruno Eck: Technische Stroemungslehre, 8. Aufalge Bd. 1 (1978), Springer Verlag Berlin, S. 137-144.

PCT International Search Report for PCT/EP2010/002294, dated Jul. 27, 2010.

Japan Search Report by Registered Searching Organization in Japanese Application No. 2012-506374, dated Jan. 10, 2014, 48 pages (with English translation).

* cited by examiner

RECEPTION MEANS FOR RECEIVING MEDICAL FLUIDS, AS WELL AS EXTERNAL FUNCTIONAL MEANS AND MEDICAL TREATMENT APPARATUS

RELATED APPLICATIONS

This application claims the benefit of U.S. Provisional Patent Application No. 61/185,607, filed on Jun. 10, 2009, which is expressly incorporated herein in its entirety by reference thereto. Further, this application claims priority to German Patent Application No. 10 2009 018 664.6, filed on Apr. 23, 2009, and German Patent Application No. 10 2009 024 466.2, filed on Jun. 10, 2009, each of which is expressly incorporated herein in its entirety by reference thereto.

FIELD OF THE INVENTION

The present invention relates to a reception means for receiving medical fluids. It further relates to an external functional means, as well as a medical treatment apparatus.

BACKGROUND

Various apparatuses such as, for example, treatment apparatuses in medical technology, comprise reception means for temporarily receiving fluids. These are generally repeatedly filled with fluid and emptied again during operation of the apparatus. Flow phenomena customarily occurring during filling and emptying are generally influenced by using suitable constructional means. Among these there are container wall nozzles, baffle walls, as well as geometrical configurations of structural elements, e.g., in immersion pipe forms, diffusor forms, and the like.

It is an object of the present invention to specify another reception means for receiving medical fluids, in particular blood, which comprises a means for influencing a fluid flow.

SUMMARY

The object of the invention is achieved through a reception means for receiving one or several medical fluids which has the features as disclosed herein.

The reception means in accordance with the invention comprises an inflow opening through which at least one medical fluid may be introduced or supplied into an interior of the reception means. It further comprises at least one fluid surge redirection element for redirecting the fluid surge of the inflowing fluid.

The expression "inflow opening" as presently used designates an opening or a recess—e.g., in a side, or lateral surface, or side wall of the reception means—through which a fluid may flow, enter, or pass into the interior of the reception means that may be closed or open towards the surroundings.

A "fluid" within the meaning of the present invention encompasses any medical liquid and/or any medical gas and/or any liquid/gas mixture (e.g., gas bubbles in liquid, foam, in particular blood including air bubbles, blood foam). In particular, it may be blood inside an extracorporeal blood circuit.

The "fluid" should here and in the following be understood to be synonymous with a medical fluid.

An "interior of the reception means" designates a volume or a capacity of the reception means which is suited and intended for being completely or partly filled with fluids and receiving them.

A "fluid surge redirection element" designates a body that is suited for influencing a fluid surge, in particular for redirecting a fluid surge impinging on it. This body may be an element adapted to be flushed and/or covered by a flow.

In terms of the invention, the fluid surge redirection element may also be understood as a fluid contact element provided inside the reception means with the purpose of being impinged by the fluid surge flowing into the interior of the reception means, or of getting into contact therewith. This contact is brought about intentionally by way of construction in order for the fluid surge to be influenced in an intentional manner. This may include a weakening of the impulse of the fluid surge, a cancellation of the impulse of the fluid surge in the sense of a transmission. In particular, it may moreover include an intentional division of the fluid surge into at least two trackable partial fluid surges or many small partial fluid surges, as will be discussed in more detail in the following.

In accordance with the invention, the fluid surge redirection element therefore comprises at least one flow-conditioning body which is adapted and/or provided and suited to divide the fluid surge into at least two partial flows. Following their division, the partial flows are present, at least temporarily, in a physically separate state, i.e., without contact among each other.

The expression "fluid surge" designates a quantity or a volume of the fluid introduced or flowing into the reception means.

The fluid surge may be a continuous and/or constant fluid surge (e.g., flowing in at a constant velocity) or a fluid surge flowing into the reception means at a particular point of time and/or only over a particular, limited time period.

The fluid surge may transmit an impulse. The fluid surge may be such that its entry into the reception means without the provision of a fluid surge redirection element in accordance with the above description would result in turbulences and/or gas inclusions (in particular inclusions of air) in the inflowing fluid (in particular a liquid) or in a fluid into which another fluid (in particular blood) is intended to flow.

The expression "partial fluid surge" designates a partial flow obtained by dividing the fluid surge originally flowing into the reception means by means of the flow-conditioning body, or a partial volume of the overall fluid surge originally having entered. The partial fluid surge represents a proportion of the fluid surge.

The occurrence of undesirable flow phenomena may advantageously be prevented by dividing the fluid surge into partial fluid surges.

In a preferred embodiment of the invention, the entirety of all the proportions of partial fluid surges obtained by means of the flow-conditioning body, which continue to remain inside the reception means following division of the fluid surge into the partial fluid surges, may add up to substantially 100% of the entire fluid surge. This means that all of the partial fluid surges continue to enter into the or initially remain inside the latter.

The proportions of the flow volume or of the flow quantity of the single partial fluid surges may be the same or may be different from each other.

In a preferred embodiment of the invention, the flow-conditioning body is disposed in an inflow region of the fluid surge, in particular in the outflow region of a phantom valve in a blood cassette for an extracorporeal blood treatment.

The expression "phantom valve" as presently used designates an element having an actor surface that may be reached by means of an actor (in the present case, for example, an actor membrane) that may fulfill the function of a valve.

The actor membrane can be made to move, dilate or curve etc. in one direction by applying a force on it, e.g., a pressing force. As a result of its movement or dilation, the actor membrane may come into contact with an element such as a sealing means, e.g., a bar, or move away from the latter. The actor membrane may thus, for example, bring about or enhance or terminate or reduce a sealing effect.

When the force acting on the actor membrane is cancelled, the latter may return, for example, to a basic position, e.g., a non-curved condition.

The expression "inflow region" designates the region of the reception means in which the fluid surge is present immediately following inflow or entry into the reception means. The inflow region may here form a region on the side of the reception means around the inflow opening in a spatial relation to the latter, in which the fluid flowing in through the inflow opening begins to spread out in the reception means and fill the reception means.

In a further preferred embodiment, the flow-conditioning body is arranged centrally (or in a central area) in the inflow region of the fluid, relative to a center axis of the inflow opening or of the direction of inflow.

Here the "center axis" designates, e.g., the one axis which is perpendicular to a central region or a center point of the cross-section of the inflow opening or to the direction of inflow such as, for example, the circle center of an inflow opening having a circular cross-section. The center axis may extend in parallel with a main direction of flow of the entire fluid surge prior to it being divided into partial fluid surges.

The expressions "central" and "middle" may be used synonymously or exchangeably in the present invention. They are intended to designate a respective arrangement of a component in a central region or in the middle of a reference system or of a reference component. A central arrangement is preferably defined such that the geometrical center, e.g., the circle center point of the cross-section of a component, is arranged on a center axis or a center point of the reference component. Geometrical center, center axis or center point may be determined in a usual manner, either geometrically or by approximation.

The expression "cross-section" as presently used may designate a cross-section perpendicular to a direction of inflow or in parallel with the latter. The "cross-section" may in the meaning of the discussion of the present invention, irrespective of additional features thereof, preferably be the cross-section of maximum diameter or maximum dimensions.

The inflow opening may be arranged, for example, in a surface interior or a center of a side, or lateral surface, or side wall of the reception means. It may, however, also be arranged in a marginal area of the side or of a limitation of the reception means.

The inflow opening may extend substantially across an entire length of a side of the reception means. Independently of this, the inflow opening may extend substantially across an entire width of the side of the reception means. It may therefore adopt different three-dimensional configurations.

In a preferred manner, however, the inflow opening is provided in a substantially centered manner in a limiting surface of the reception means, i.e., the center point (e.g., the circle center point of an inflow opening having a circular cross-section) of the inflow opening may be arranged at half the length and/or half the width of the lateral surface of the reception means.

The inflow opening may have a circular or an elliptic cross-section; however, it may equally have any other cross-section appearing appropriate for the purposes of the present invention.

Several inflow openings configured in the same manner or differently may furthermore be provided in the reception means. Their respective configuration may be selected to be rheologically optimized and appropriate for the desired purpose.

Where several inflow openings are provided in one or several side walls or lateral surfaces of the reception means, at least one of the inflow openings may in accordance with the invention comprise a fluid surge redirection element or a flow-conditioning body in the inflow region of the fluid surge.

The flow-conditioning body may preferably have a symmetrical configuration. The flow-conditioning body may preferably have a symmetrical configuration or arrangement relative to the center axis of the inflow opening.

This encompasses the possibility of a cross-section of the flow-conditioning body being arranged or provided symmetrically relative to the center axis of the inflow opening in a plane perpendicular to the direction of inflow of the fluid surge introduced into the reception means. In a preferred manner, symmetry is provided in the closer vicinity of the fluid surge element. The entire means need, however, not inevitably be symmetrical.

The flow-conditioning body may generally have a front or impact surface on which the entering fluid surge or a substantial portion thereof impinges, and a rear side at which the partial fluid surges may be combined.

A recombination of the divided partial fluid surges on a rearward portion of the flow-conditioning body or at a downstream portion thereof is encompassed by the invention. The invention is, however, not restricted to a recombination; in other words, this is not a necessary effect of every embodiment of the invention.

The flow-conditioning body may furthermore have a left and a right lateral flank along which respective partial fluid surges may flow.

A flow-conditioning body having a symmetrical configuration may be configured such that the geometrical shape or configuration of the left and right lateral flanks is provided to be mirror-symmetrical relative to the center axis of the inflow opening.

The geometrical shape of the front and rear sides of the flow-conditioning body may equally be arranged to be mirror-symmetrical relative to an axis that is perpendicular to the center axis of the inflow opening, i.e., perpendicular to the direction of flow of the fluid surge entering into the reception means. The invention is, however, not restricted to this.

For instance, the cross-section of the flow-conditioning body may be circular, with the flow-conditioning body itself having a rotationally symmetrical configuration in this case.

As an alternative, the cross-section of the flow-conditioning body may have an elliptical configuration, in which case the respective left and right lateral flanks of the flow-conditioning body are configured to be symmetrical relative to each other, as well as the front and rear sides of the flow-conditioning body.

The cross-section of the flow-conditioning body may also have a paraboloid or ogival or other configuration.

The cross-section of the flow-conditioning body may change along the height or depth of the flow-conditioning body. For instance, the cross-sectional area may vary across the height of the flow-conditioning body, e.g., the cross-sectional area or a diameter thereof may diminish across the height, i.e., become smaller or reduced. The cross-section of the flow-conditioning body may, however, also remain constant along the height or depth of the flow-conditioning body.

The cross-sectional area or the diameter may repeatedly diminish and increase (or vice versa) across the height of the flow-conditioning body in order to obtain a fluid surge redirection that is optimized for the respective application and the respective fluid used.

The flow-conditioning body may be configured for subdividing the fluid surge originally introduced into the reception means into more than two partial fluid surges.

The flow-conditioning body may, for example, comprise a passage opening in a central region for passing through a third partial fluid surge.

The passage opening may extend, for example, from the front to the rear side of the flow-conditioning body.

In a further preferred embodiment, the flow-conditioning body is disposed in the inflow region of the reception means while being spaced apart from the inflow opening by 0.4 to 2 times the diameter of the inflow opening or of the flow passage.

This spacing may preferably refer to a distance between the inflow opening, for example the mouth of the inflow opening in the lateral surface or side wall of the reception means, and the front (e.g., the point located furthest in an upstream direction from the fluid surge or from the one main point of impact of the fluid surge) of the flow-conditioning body.

In another preferred embodiment, a diameter of the flow-conditioning body in a plane perpendicular to the center axis or perpendicular to the main direction of impact of the fluid surge onto the flow-conditioning body may be 0.4 to 1.2 times the size of the diameter of the inflow opening or of the flow passage.

Figure 1:
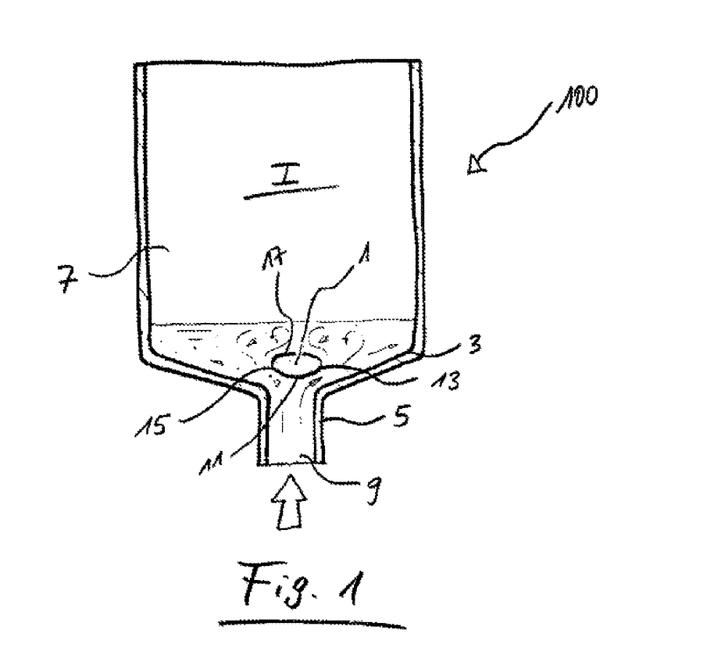
FIG. 1 is a top view of the reception means of the invention of a first embodiment in a first condition.

This diameter may preferably be the maximum diameter of the flow-conditioning body, for example the longer diameter of a flow-conditioning body having an elliptical cross-section as shown in FIG. 1.

In a further preferred embodiment, the fluid surge redirection element is realized in material connection or integrally formed with the reception means.

The fluid surge redirection element or the flow-conditioning body may be realized or formed jointly with the reception means during the manufacture of the latter. This may, for example, be obtained by means of injection molding of the reception means. The reception means may, for example, be configured as a prismatic injection-molded chamber.

The reception means may be realized in a cassette design or as a part of such a cassette. It may, for example, be an external functional means or part of an external functional means. The reception means may preferably be integrated into the external functional means by material connection.

In a further preferred embodiment, the reception means is connected to an inflow passage at the inflow opening. It may alternatively be connected to several inflow passages. The connecting passage or inflow passage may be integrated into the lower end of the reception means integrally or by material connection.

The inflow passage may be a closed, a semi-open passage, or a conduit. It may be integrated into an external functional means. Such a passage or such a conduit may be realized or formed during manufacture of the external functional means, for example by means of injection molding.

In a further preferred embodiment, the inflow opening may be suited and intended to allow fluids having entered into the interior of the reception means to flow out. Various (in a given case also different) inflow and outflow passages or various (in a given case also different) inflow/outflow passages may, however, also be provided.

This may, for example, be advantageous for achieving an exchange of fluids as complete as possible during filling or emptying of the reception means.

This may in particular be advantageous when the reception means is part of an external functional means such as, for example, a blood cassette or blood treatment cassette, and a space-saving arrangement of the single components of the blood cassette is crucial or necessary or desired.

In order to adjust a direction of flow of the fluids flowing into or flowing out of the reception means, the inflow or outflow opening may, for example, be provided in the very opening, i.e., in the passage surface of the latter, with one or several different and/or variously or differently configured or provided projections, indentations, flow elements or flow conditioning elements, and the like.

For the purpose of complete emptying of the reception means by downward draining of the liquid (emptying by gravity), the drainage passage or the outflow passage may be arranged at the geodetically lowest point of the reception means.

In the surroundings of the drainage passage or outflow passage, the side walls of the reception means may have a certain minimum inclination which may facilitate the outward flow of the fluids present in the reception means. Thus, even a reception means having an imperfectly vertical orientation may advantageously also run empty.

Furthermore, dead flow zones may advantageously be reduced or even avoided with such an arrangement.

In another preferred embodiment, the reception means is arranged inside an extracorporeal blood circuit.

The fluid surge redirection element, in particular a blood surge redirection element or blood surge element, may be suited and intended for achieving a flow deceleration, for generating a turbulence and/or redirecting a blood surge present in a single-needle chamber, or for cancelling the impulse of the blood surge. A like blood surge redirection element may in particular have a rheologically optimized configuration. It may, for example, be configured in the shape of an ellipsoidal or round column which is connected to a wall of the single-needle chamber on at least one portion of its circumference.

Without a blood surge redirection element, a blood surge flowing in through the phantom valve might in a given case cause gushing. This might lead to hunting or sloshing movements, respectively, of the liquid level and/or to foam formation. By means of the blood surge element the total blood surge is divided into two smaller blood surges, whereby the impulse of the total blood surge may be cancelled, and gushing, sloshing movements and/or foam formation may advantageously be avoided.

The object of the invention is also achieved through an external functional means. All of the advantages achievable by means of the reception means of the invention may also be achieved with the external functional means of the invention.

An external functional means of the invention comprises at least one reception means in accordance with the invention.

The external functional means of the invention may be intended for use in a treatment method, in particular in an extracorporeal blood treatment method. Treatment methods within the meaning of the present invention include medical treatment methods—in particular blood treatment methods such as dialysis methods, methods of laboratory technology, methods of food or drug manufacture, and the like.

In a preferred embodiment, the external functional means of the invention is configured as a blood cassette.

The external functional means may be intended for use in or on a treatment apparatus.

The external functional means may be provided with a cover member on at least one side.

A "cover member" may, for example, be a membrane, a film, and the like. Exemplary embodiments for suitable cover members as well as their realization and arrangement on the external functional means may, for example, be taken from German Patent Application No. 10 2009 012 632.5 (representative's file FM19A25) as filed with the German Patent and Trademark Office on Mar. 10, 2009 by the applicant of the present invention and having the title "Abdichtungseinrichtung zum Abdichten eines Volumens einer medizinischen Behandlungsanordnung gegen ein weiteres Volumen sowie Anordnung and Verfahren" [A sealing means for sealing a volume of a medical treatment arrangement against another volume, as well as an arrangement and a method], the relevant disclosure of which is herewith fully incorporated by way of reference.

The cover member of the external functional means may preferably be arranged or provided such that it rests on an upper side of the flow-conditioning body, in particular on a sealing bar peripherally provided on the upper side of the flow-conditioning body.

In this way, it may be possible to achieve a fluid-tight seal of the external functional means against an outside, wherein the upper side of the flow-conditioning body is capable of providing another point of support.

Concurrently, the sealing between the sealing means and the upper side of the flow-conditioning body may provide sealing for the fluid present in the interior of the reception means, so that it may not leak out of the reception means at the upper side of the reception means into other compartments of the external functional means and/or to an outside of the external functional means.

The external functional means may, for example, be configured as a blood cassette as described in German Patent Application Nos. 10 2009 018 664.6 (representative's file FM19A27) and 10 2009 024 468.9 (09/33-d01; FM19B27 DE) filed with the German Patent and Trademark Office on Apr. 23, 2009 and Jun. 10, 2009 by the applicant of the present invention, respectively, each having the title Externe Funktionseinrichtung, Blutbehandlungsvorrichtung zum Aufnehmen einer erfindungsgemäßen externen Funktionseinrichtung, sowie Verfahren" [External functional means, blood treatment apparatus for receiving an external functional means in accordance with the invention, and method]. The relevant disclosures of these are herewith fully incorporated by way of reference.

Such an external functional means may be a single-use component or a single-use article.

The external functional means may, for example, be made of a plastic material.

The external functional means may be configured as an injection-molded hard part having a cover means, e.g., a film, welded on.

The object of the invention is also achieved through a medical treatment apparatus. All the advantages that may be achieved with the reception means of the invention may also be achieved with the treatment apparatus of the invention.

The treatment apparatus of the invention may comprise at least one reception means in accordance with the invention and/or at least one external functional means in accordance with the invention.

The treatment apparatus may be employed in a treatment method as specified in the foregoing.

For instance, the treatment apparatus may be a blood treatment apparatus such as a dialyzing apparatus for performing a dialysis treatment such as a hemodialysis, a hemofiltration, a hemodiafiltration, and the like.

The present invention may advantageously be suited and intended for calming a fluid flow or fluid surge flowing into a reception means.

This may in particular be advantageous when the reception means has a clearly larger cross-section than the cross-sections of tubings, pipes, passages or valves through which fluids are introduced or fed into the reception means.

With the present invention, it may advantageously be possible to avoid the turbulences and/or inhomogeneities usually occurring upon passage through steps or changes in cross-sections, both within the flowing volume and also on a free surface (e.g., a level surface) towards a gas-filled space or on the fluid-wetted surfaces of the passages, reception means and/or further built-in elements, and the like.

Advantageously, turbulences that are usually created when fluids flow in or out during filling and/or emptying processes may equally be reduced or even be avoided entirely by means of the present invention.

With the present invention, it may advantageously be possible to avoid stirring in, introduction or encapsulation of gas bubbles such as, for example, air bubbles, and/or foam formation, in the fluids flowing into or already present inside the reception means. In particular, it is advantageously possible to reduce or avoid air inclusions in the phases of wetting of and detachment from the side walls of the reception means.

Sloshing and/or foaming level surfaces of the fluids as well as impacting flows and/or undesirable sloshing and/or rotational flows may advantageously be reduced or avoided in the reception means in accordance with the invention as a result of dividing the fluid surge entering into the reception means.

As the formation of sloshing movements, undulations and/or eddies in the liquid surface is reduced or does not appear, it is possible to avoid further gas contact and/or gas absorption while, e.g., enabling an accurate measurement of the filling level of the liquid.

In contrast with conventional, built-in flow-calming elements or conformations for reception means, an impairment of the functional possibilities of the sensor elements may advantageously be avoided in the present invention.

This may, for example, advantageously contribute to being able to carry out sufficiently accurate measurements on the fluids present in the reception means such as, for example, a measurement of the filling level of the fluids as accurate as possible.

Furthermore, it is possible—for example when measuring a property of the fluids present in the reception means—to avoid the risk or the problem of obtaining distorted measurement results caused by the occurrence of gas bubbles or air bubbles or swirls.

In contrast with large-dimensioned devices or means from the prior art such as, for example, a diffusor form of the passages—which in many cases requires diffusor lengths of more than ten times the passage cross-section—, an immersion pipe form of the inflow passage or outflow passage, a container wall nozzle and/or baffle walls, the present invention may be provided as a reception means inside an external functional means that is minimally-invasive, small-dimensioned and arranged so as to not cause any interference.

The fluid surge redirection element may advantageously consist of only one component required for its function, i.e., the flow-conditioning body.

In many cases, the fluid surge redirection element may advantageously represent not a separate component but a geometrical configuration as a geometry integrated into a wall of the inflow passage and/or a side wall of the reception means that is free from additional costs, installation spaces, joints and/or dead spaces.

The flow-conditioning body may advantageously be realized in a simple and/or cost-efficient manner by an injection molding technique, without requiring additional slides and/or mold cores having locations of passage through the mold insert that need to get into contact with a fluid later on. Hereby, the introduction of impurities from the movable seams of an injection molding tool into the fluid-wetted surface of the reception means may advantageously be prevented.

The flow-conditioning body may advantageously be realized with a low demand of additionally required constructional height, additional volume and/or additional surface— in comparison with a reception means lacking built-in flow-calming elements or having built-in flow-calming elements other than the flow-conditioning body of the invention.

The small surface and/or the rheologically favorable conformation of the flow-conditioning body may in a further advantageous manner lead to flow calming with minimized introduction of air, adhesion of air, shear rate and/or dead flow spaces.

The flow-conditioning body may moreover bring about advantages precisely also in the wetting and detachment phases in which the liquid level still just about encompasses or relinquishes the flow-conditioning body. Thus, for example, during draining of the fluids, the flow-conditioning body may advantageously only leave a small and reproduceable quantity of fluids for adhesion to the flow-conditioning body, which may have an advantageous effect on level measurements and on the fluidic method (complete exchange of fluid).

The small surface of the flow-conditioning body, the absence of sharp edges and/or hollow spaces and/or the low formation of turbulences and/or foam formation may advantageously lead to a high blood compatibility of the flow-conditioning body.

At a low space demand, the flow-conditioning body may be arranged closely in front of the inflow and/or outflow passage leading to the container. Measurement means detecting, for example, levels, foam, phase boundaries and/or air bubbles, may advantageously be arranged without interference and/or built-in elements in the level space of the reception means situated above, and utilize this space which is substantially not relevant for the fluids.

Further features and aspects of example embodiments of the present invention are described in more detail below with reference to the appended Figures.

DETAILED DESCRIPTION

In the following, the present invention shall be described by referring to the appended drawings. In the drawings, identical reference numerals designate same or identical elements.

FIG. 1 shows a reception means of the invention of a first embodiment in a filling phase.

In its interior I, the reception means 100 of the invention comprises a fluid surge redirection element comprising a flow-conditioning body 1.

The flow-conditioning body 1 is disposed within a transitional area 3 of the reception means 100 between an inflow passage 5 and a utilization region 7 of the reception means 100.

The transitional area 3 of the reception means 100 allows a reasonable transition between the relatively small fluid cross-section of the inflow passage 5 and the relatively large cross-section of the reception means 100 as a result of, for example, the ability to manufacture the reception means 100 and the inflow passage 5 in one piece, good self-emptying of the reception means 100 even in the case of an obliquely oriented arrangement of the reception means 100, the integration of a passage closure valve immediately at the transition of the inflow passage 5 into the reception means, and the like.

For example, measurement means for detecting a filling level of the fluids present in the reception means 100 may be provided in the transitional area 3. Such measurement means may be configured in a manner particularly optimized for these detection purposes.

The flow-conditioning body 1 is preferably disposed inside the transitional area 3, also for the purpose of utilizing the space of the transitional area 3.

The utilization region 7 of the reception means 100 may satisfy demands such as, for example, a favorable ratio between required space and filling volume of the reception means 100, a favorable measuring capability of the filling volume of the reception means 100 or of the fluids present therein or other quantities (e.g., by means of the transparency of the fluids present in the reception means 100), a small wetted surface relative to the filling volume, good wetting and detachment behavior, a good drainage property of the fluids, and the like.

A fluid surge (in FIG. 1 designated by a block-type arrow) flows into the reception means 100 through an inflow opening 9.

The fluid surge flowing into the reception means 100 impinges on a front 11 of the flow-conditioning body 1 and is divided into two partial fluid surges. The partial fluid surges are passed along a right lateral flank 13 and a left lateral flank 15, respectively.

On a rear side 17 of the flow-conditioning body 1 the partial fluid surges meet again or come together.

In accordance with the representation in FIG. 1, the flow-conditioning body 1 may have an elliptical cross-section.

In accordance with the representation in FIG. 1, the flow-conditioning body 1 is arranged substantially symmetrically in the inflow zone of the fluid surge.

The dimensioning of both width and height (extension in the direction of flow in the direction of the double arrow) of the flow-conditioning body 1 may be intended to give the flow-conditioning body 1 a smallest possible dimension in all of the directions in space. These minimally small dimensions of the flow-conditioning body 1 may preferably contribute to ensuring a least possible loss of useful filling volume of the reception means 100, and/or to reducing the surface of the reception means 100 to be wetted and de-wetted.

Such a minimization of surface may favor the arrangement of the fluids in accordance with the invention in several points: a smaller surface may advantageously lead to less possibilities of adhesion for small gas bubbles. Further, a smaller surface may generally reduce the chemical and/or physical reactivity of the fluids with the material of the reception means 100 and/or with the gas present in the reception means. This may, for example, advantageously lead to improved hemocompatibility and/or a reduced clotting tendency of blood flowing in due to less air and less foreign surface.

A smaller surface may advantageously allow the fluids to flow into the reception means 100 and out of it, respectively, in a more complete and reproduceable manner—in relation to the maximum filling volume—, since smaller residual quantities may become adhered to this surface. An accurate measurement of the filling volume with the aid of the filling level may be facilitated.

The exchange of fluids between the filling/emptying cycles may advantageously take place in a more complete manner. Blending of the fluid charges—which may in many cases be desired in terms of method technology—may in particular also be achieved with regard to an improved hemocompatibility by avoiding adhesion of blood and reduction of the retention time of blood on foreign surfaces.

The minimum dimensions of the flow-conditioning body 1 may be determined by way of experiment and selected such that the desired effect of calming the flows and the level surface, as well as minimum generation and stirring in of gas into the fluids flowing into the reception means 100 may be attained.

The smallest possible dimensions may depend: a) on the shape and/or the mean flow velocity in the inflow passage 5; b) on the composition and viscosity of the inflowing fluids; c) on the material and the surface structure of the side walls of inflow passage 5, reception means 100 and/or flow-conditioning body 1; d) on the configuration of the transitional area 3; e) on the geometry of coupling of the flow-conditioning body 1 to the reception means 100; f) on the possible pulsation and the admissible volume flow range of the inflowing fluids; and/or g) on any geometrical factors of influence on the flows in the closer and also somewhat further surroundings (up to about ten times the cross-section of the inflow passage 5) of the flow-conditioning body 1.

The desired effect of flow calming may advantageously already be obtained at surprisingly small dimensions of the flow-conditioning body 1, in the range of dimensions smaller than the central cross-section of flow in the inflow passage 5.

Figure 3:
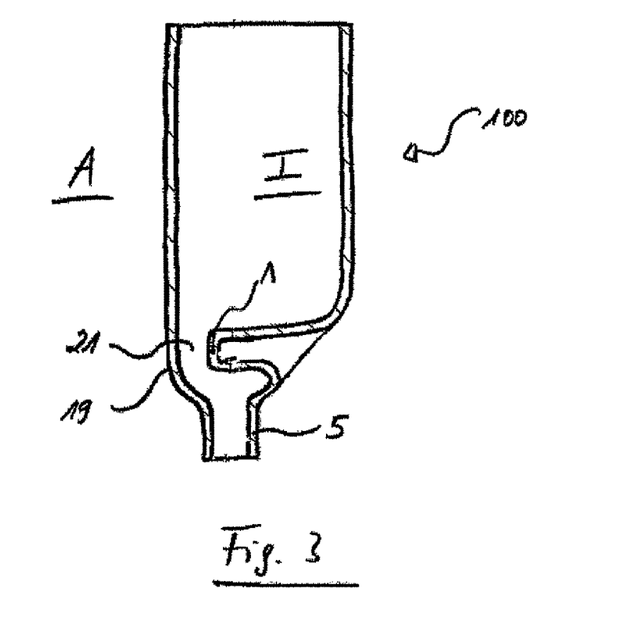
FIG. 3 is a longitudinal sectional view of a reception means in accordance with the invention.
Figure 4:
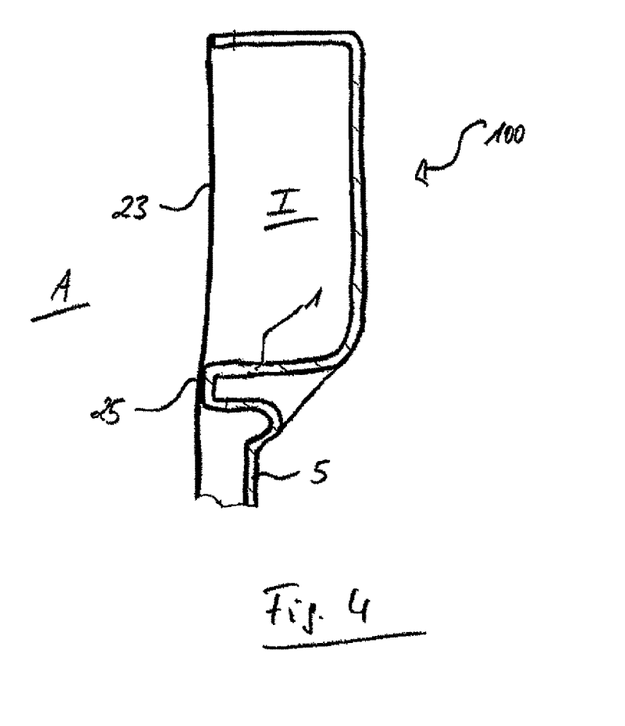
FIG. 4 is a longitudinal sectional view of the reception means of the invention in accordance with another embodiment.

The flow-conditioning body 1 may be curved in all of its dimensions like, e.g., a sphere or an ellipsoid. In order to achieve the manufacturing capability of the flow-conditioning body 1, coupling to the reception means 100 without joints and/or dead spaces and/or the low-cost integral manufacturing with the reception means 100, the flow-conditioning body 1 may in a particularly preferred embodiment have a flow-conditioning cross-section curved in only two directions in space. It may, for example, preferably possess a substantially prismatic constructional shape as represented in FIGS. 3 and 4, described in greater detail below.

Due to the division of the fluid surge originally flowing into the reception means 100 into at least two partial fluid surges, flow-calming of the fluid surge may take place. In comparison with other solutions, the effective mechanism of flow-calming may be based in a higher extent on an intentional self-cancellation of the surge. On the whole, it may represent a combination of several rheological effects.

As is also illustrated in FIG. 1, a deceleration of the flow of the fluid surge may be achieved a) by widening a passage of the inflow passage 5 between the flow-conditioning body 1 and the walls, or side walls, of the transitional areas 3 and/or b) by a subdivision into at least two same-quantity partial flows or partial fluid surges of a respective half quantity which continue their flow in opposite directions and/or c) by subdividing the respective partial fluid surges into at least two further partial fluid surges each having an opposite impulse or spin due to adhesion to the flow-conditioning body 1 on the one side and to the respective side wall of the reception means 100 on the other side and/or d) by the opposed, same-quantity flow and spin impulses meeting and cancelling each other on the far side, i.e., the rear side 17 of the flow-conditioning body 1, and/or e) by the opposed, same-quantity flow impulses meeting and cancelling each other in the regions between the flow-conditioning body 1 and a side wall of the reception means 100 to the right and left of the flow-conditioning body 1, and/or f) by annihilation of flow energy due to frictional effects among the multiple partial flows or partial fluid surges having respective opposite directions of flow and rotation.

Observations allow the conclusion that the reception means 100 of the invention having the surge-calming or surge-cancelling arrangement may even exert an additional calming effect on turbulences and/or hunting or sloshing oscillations of the level surface introduced otherwise (such as by shocks to the reception means).

The flow-conditioning body 1 may have a circular, elliptical, paraboloidal, or ogival cross-section. The flow-conditioning body 1 may have a non-symmetrical cross-section relative to the sides facing the inflow passage 5 and the sides facing away from it.

The symmetrical configuration of the geometry at the right lateral flank 13 and at the left lateral flank 15 may be essential for the correct functioning of the impulse-dividing and inherent impulse-cancellation processes.

For a minimization a) of volume, b) of the demand on structural height and/or c) of the surface of the flow-conditioning body 1, a substantially transversely elliptical shape of the flow-conditioning body 1 was found to be advantageously effective.

Depending on the fluids present, it may, however, be reasonable to provide the curvatures on the side of the flow-conditioning body 1 facing the inflow passage 5 differently from the curvatures on the side of the flow-conditioning body 1 facing away from the inflow passage 5.

Figure 2:
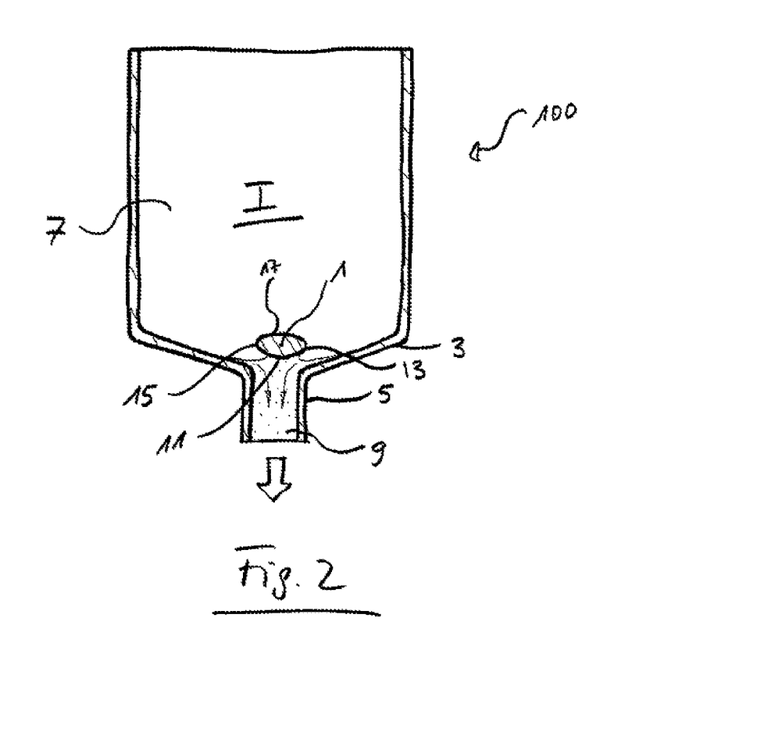
FIG. 2 is a top view of the reception means of the invention of FIG. 1 in a second condition.

FIG. 2 shows the reception means 100 of the invention in an emptying phase in which the fluids are in a state immediately before detachment from the flow-conditioning body 1.

The inflow passage 5 here has the function of an outflow passage.

As may be seen in FIG. 2, the right/left symmetrical realization of the flow-conditioning body 1 and/or of the remaining reception means 100 in combination with the gradual widening of the cross-section of flow of the outflow passage before and behind the narrowest zone of passage to the right and left of the flow-conditioning body 1 may contribute to the compact zone of the main fluid staying for as long as possible in contact with the thin fluid zones of residual wetting with the flow-conditioning body 1 and/or with the side walls of the reception means 100. Here, a maximum possible quantity of residual liquid is entrained with the main flow before detachment from the surfaces of the flow-conditioning body 1 and from the side walls of the reception means 100 occurs and residual films remain thereon.

FIG. 3 shows an embodiment of the reception means in accordance with the invention in a longitudinal sectional view, wherein the reception means 100, the inflow passage 5, and the flow-conditioning body 1 are injection-molded into a single piece.

In the embodiment shown, the flow-conditioning body 1 is not connected to an opposite wall 19 on its end side but has a sufficiently large gap 21 from the wall 19 in order to avoid dead flow zones and/or nests of air.

FIG. 4 shows another embodiment of the present reception means 100 in a longitudinal sectional view, wherein the overall arrangement is realized in the typical cassette design.

In such a cassette design, passages such as, for example, an inflow passage 5 and/or chambers in an injection-molded part may substantially be formed to be open on one side. A cover means 23 designed to be flat and/or equally having semi-open structures, for example a lid or a film, may fulfill the task of closing the chambers and/or passages against an outside A. In the embodiment with a film closure, the film—as is shown in FIG. 4—may be applied on an end face 25 of the flow-conditioning body 1 in direct contact with the latter by welding and/or pressing. In such an arrangement, a gap may intentionally be avoided.

Figure 5:
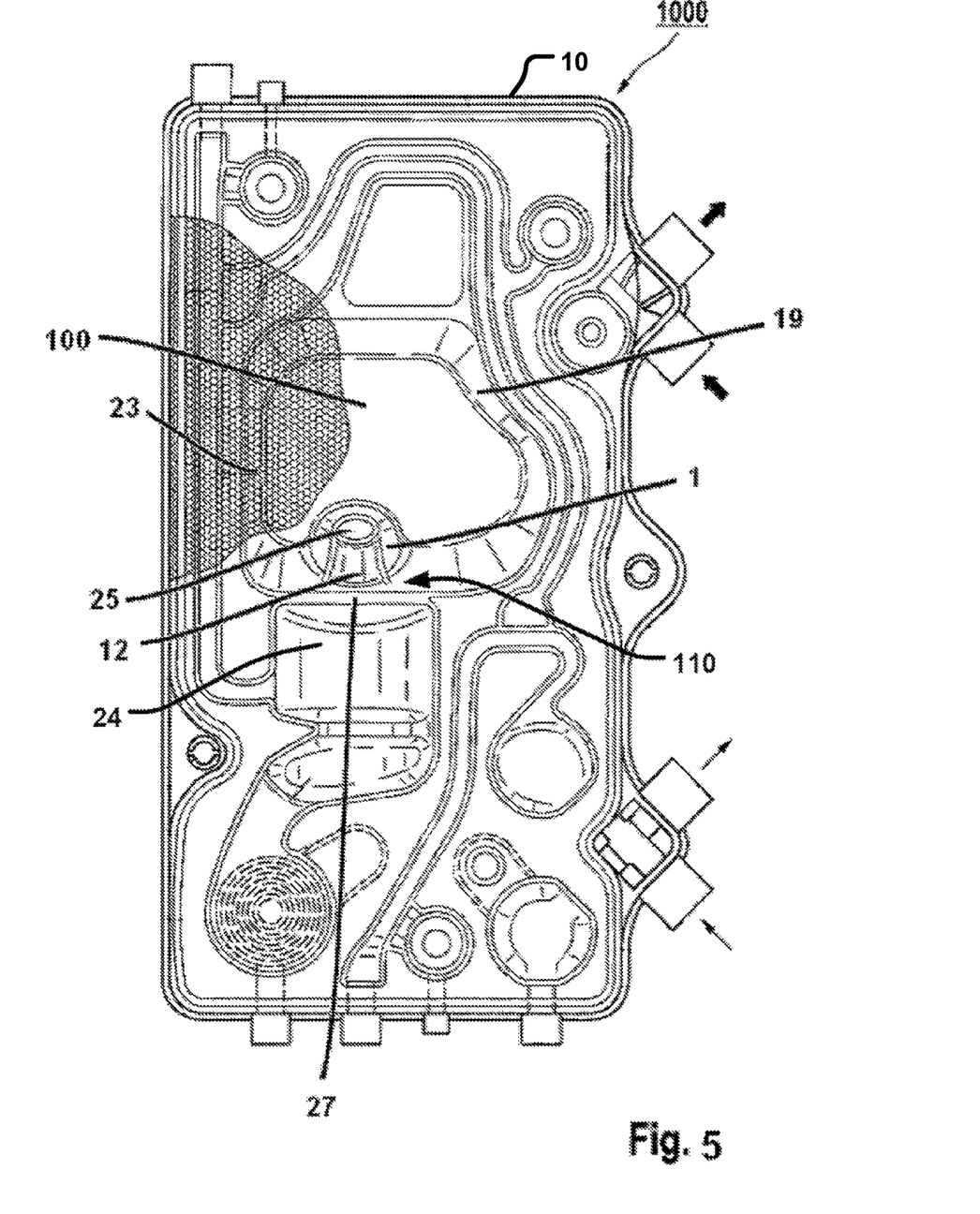
FIG. 5 is a front view of a functional means of the invention in accordance with a preferred embodiment that is provided with a cover means at its front side.

FIG. 5 shows a front view of an external functional means in accordance with the invention which is provided with a cover or cover means 23 at the surface one looks upon in FIG. 5.

The external functional means is here exemplarily configured as a blood treatment cassette 1000 comprising a rigid body (hard part 10) having a plurality of walls that define chambers, passages, valves, and the like. The cover means 23 covers a front side of the blood treatment cassette 1000. By way of example, it is realized in the form of a flexible membrane or film.

The blood treatment cassette 1000 may be coupled to a blood treatment apparatus (not shown in FIG. 5) at least by the front side shown in FIG. 5.

The blood treatment cassette 1000 comprises the reception means 100 in accordance with the invention.

The reception means 100 extends from the front view shown in FIG. 5 to the rear into the plane of drawing of FIG. 5. The extension of the wall 19 of the reception means 100 away from the observer is indicated by outwardly radiating lines. The flow-conditioning body 1 extends from its base in a direction towards the observer of FIG. 1.

The reception means 100 comprises the flow-conditioning body 1. In FIG. 5, the elements of the flow-conditioning body 1 that may be seen particularly well are the end face 25 as well as a saddle-type connecting region 12 situated deeper in the plane of drawing between flow-conditioning body 1 and wall 19.

The reception means 100 comprises a phantom valve 27 at its lower end, i.e., at the area of flow impingement 110. The flow-conditioning body 1 in the reception means 100 is impinged by the flow that enters the reception means 100 via the phantom valve 27, wherein blood from the chamber 24 situated below (e.g., a venous blood chamber as described in the application (09/34-d04 DE; 11FM19A33) filed with the German Patent and Trademark Office on Jun. 10, 2009 by the applicant of the present application and having the title "Luftabscheider, externe Funktionseinrichtung, Blutkreislauf sowie Behandlungsvorrichtung" [Air separator, external functional means, blood circuit, and treatment apparatus], the relevant disclosure of which is herewith fully incorporated by way of reference thereto) flows into the reception means 100 through the phantom valve 27 (i.e., a passage formed between a first portion of the flexible membrane cover means 23 and a bar portion of the blood treatment cassette 1000).

Figure 6:
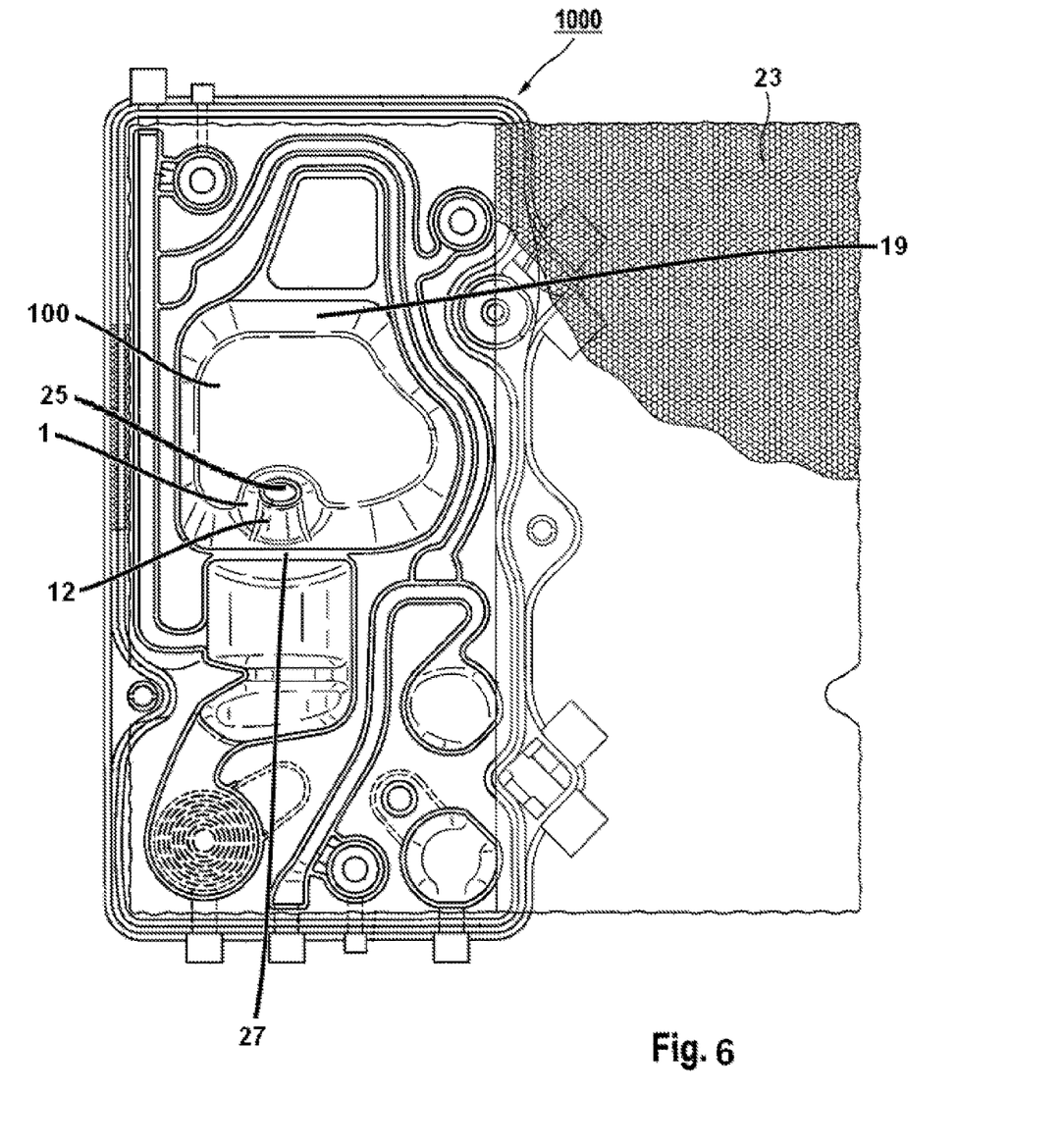
FIG. 6 shows the external functional means of FIG. 5 with the cover means swung open following destructive cutting.

FIG. 6 shows the blood treatment cassette 1000 of FIG. 5, with the cover means 23 visible at the left-hand margin of the blood treatment cassette 1000 while having been cut open destructively at the top and bottom and swung open to the right.

FIG. 6 shows the elements inside the blood treatment cassette 1000 that are visible in more detail after having cut open the film.

In order to avoid repetitions, reference is made to the configurations of the individual elements as discussed in the foregoing for the description of FIG. 5.

Figure 7:
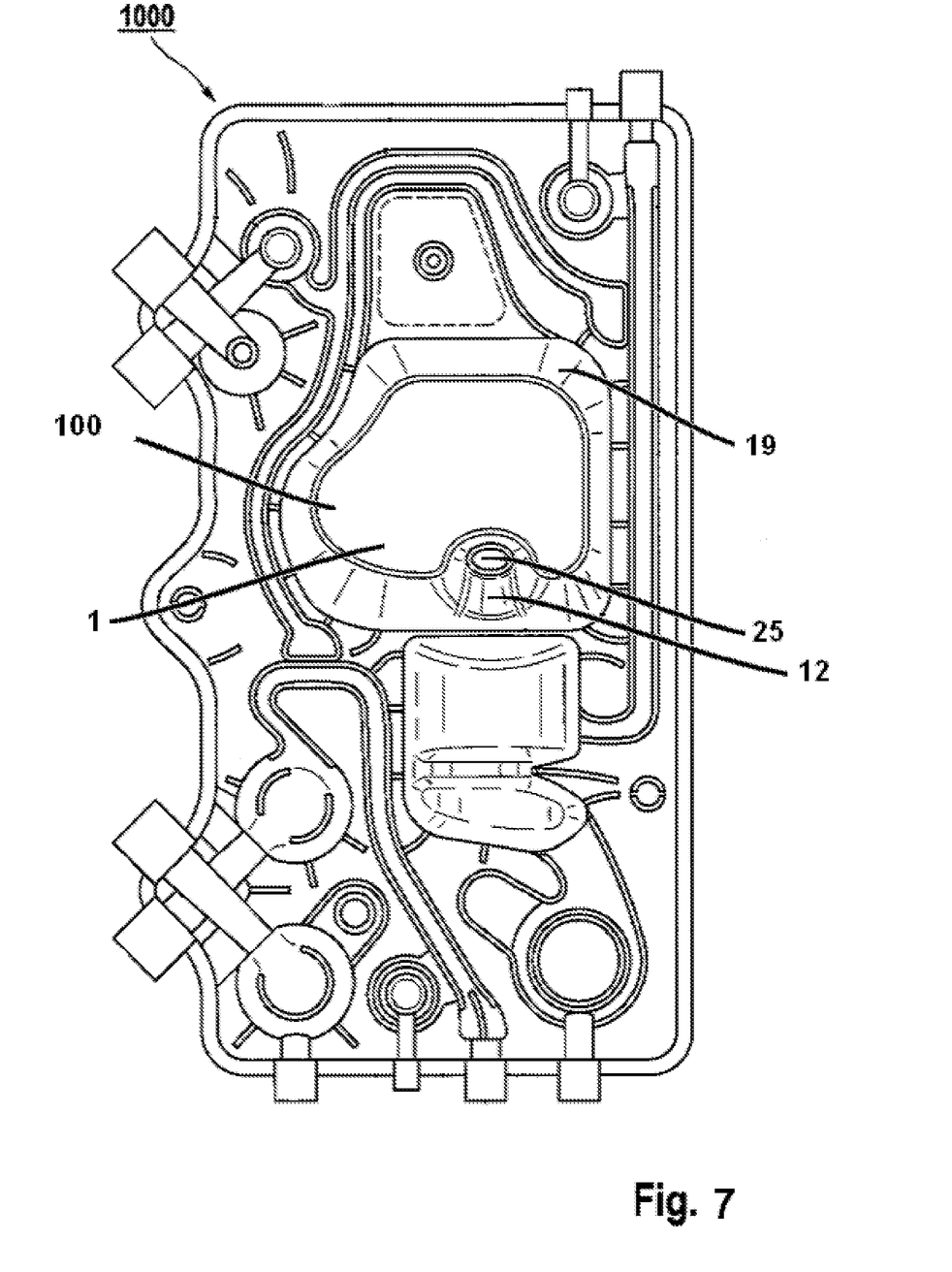
FIG. 7 shows the external functional means of FIG. 5 and FIG. 6 when viewed from its rear side.

FIG. 7 shows the blood treatment cassette 1000 from its rear side. When the blood treatment cassette 1000 is coupled to the blood treatment apparatus, an observer opening a door of the blood treatment apparatus for removing the blood treatment cassette 1000 will look upon this rear side.

With regard to further details for the blood treatment cassette 1000, reference is made to its detailed description in the above-named application directed to it, the contents of which are herewith fully incorporated into the present description.

| List of Reference Numerals | |
| --- | --- |
| Reference Numeral | Description |
| 100 | reception means |
| 1000 | blood treatment cassette |
| 1 | flow-conditioning body |
| 3 | transitional area |
| 5 | inflow passage |
| 7 | utilization region |
| 9 | inflow opening |
| 11 | front of the flow-conditioning body |
| 12 | saddle-type connecting region |
| 13 | right lateral flank of the flow-conditioning body |
| 15 | left lateral flank of the flow-conditioning body |
| 17 | rear side of the flow-conditioning body |
| 19 | wall of the reception means |
| 21 | gap |
| 23 | cover means |
| 25 | end face of the flow-conditioning body |
| 27 | phantom valve at the area of flow impingement |

What is claimed is:
1. A blood treatment cassette comprising:
a rigid body having a plurality of walls;

a flexible membrane attached to the rigid body and cooperating with the plurality of walls of the rigid body to define a liquid-receiving interior space and a single passage that permits liquid to flow therethrough into and out of the interior space, a first portion of the flexible membrane being movable relative to a first portion of the rigid body along a peripheral portion of the interior space, the first portion of the flexible membrane and the first portion of the rigid body being configured to define the single passage that permits liquid to flow therethrough into and out of the interior space when the first portion of the flexible membrane is spaced apart from the first portion of the rigid body, the first portion of the flexible membrane and the first portion of the rigid body being configured to prevent liquid from flowing into or out of the interior space when the first portion of the flexible membrane is held in contact with the first portion of the rigid body, and the flexible membrane being attached to the rigid body in a manner such that liquid can flow into or out of the interior space only when the first portion of the flexible membrane is spaced apart from the first portion of the rigid body to define the single passage that permits liquid to flow therethrough into and out of the interior space; and a flow-conditioning member extending from the rigid body into the interior space adjacent the first portion of the rigid body, the flow conditioning member being configured such that liquid impinges the flow-conditioning member when the liquid flows into the interior space via the single passage that permits liquid to flow into and out of the interior space.

2. The blood treatment cassette according to claim 1, wherein the flow-conditioning member is arranged centrally relative to a center axis of the single passage that permits liquid to flow therethrough into and out of the interior space.

3. The blood treatment cassette according to claim 1, wherein the flow-conditioning member has a symmetrical configuration.

4. The blood treatment cassette according to claim 3, wherein the flow-conditioning member has a circular cross-section.

5. The blood treatment cassette according to claim 3, wherein the flow-conditioning member has an elliptical cross-section.

6. The blood treatment cassette according to claim 3, wherein the flow-conditioning member has a paraboloidal cross-section.

7. The blood treatment cassette according to claim 3, wherein the flow-conditioning member has an ogival cross-section.

8. The blood treatment cassette according to claim 1, wherein the flow-conditioning member is arranged at a distance from the single passage that permits liquid to flow therethrough into and out of the interior space of 0.4 times to 2 times a width of the single passage that permits liquid to flow therethrough into and out of the interior space.

9. The blood treatment cassette according to claim 1, wherein a width of the flow-conditioning member in a plane perpendicular to a center axis of the single passage that permits liquid to flow therethrough into and out of the interior space is 0.4 to 1.2 times a width of the single passage that permits liquid to flow into and out of the interior space.

10. The blood treatment cassette according to claim 1, wherein the flow-conditioning member is formed as a single piece of material with the rigid body.

11. The blood treatment cassette according to claim 10, wherein the single piece of material is injection-molded.

12. The blood treatment cassette according to claim 1, further comprising a chamber adjacent the single passage that permits liquid to flow therethrough into and out of the interior space and at an opposite side of the single passage that permits liquid to flow into and out of the interior space in comparison to the interior space, wherein the rigid body and the flexible membrane cooperate to define the chamber.

13. The blood treatment cassette according to claim 12, wherein the chamber is in fluid communication with a first fluid passage and a second fluid passage, and wherein each of the first fluid passage and the second fluid passage terminate at a respective connector located at a periphery of the rigid body.

14. The blood treatment cassette according to claim 1, wherein the flexible membrane is attached to the flow-conditioning member.

15. The blood treatment cassette according to claim 1, wherein the flexible membrane rests on an upper side of the flow-conditioning member.

16. The blood treatment cassette according to claim 1, wherein the first portion of the flexible membrane is adapted to be held in contact with the first portion of the rigid body by application of a pressing force on the first portion of the flexible membrane.

17. The blood treatment cassette according to claim 1, wherein the rigid body comprises an injection-molded hard part and the flexible membrane comprises a film welded thereon.

18. The blood treatment cassette according to claim 1, wherein the blood treatment cassette is arranged in an extracorporeal blood circuit.

19. An external functional means for treating at least one fluid, the external functional means comprising the blood treatment cassette according to claim 1.

20. A medical treatment apparatus for treating at least one fluid, the medical treatment apparatus comprising the external functional means according to claim 19.

21. The medical treatment apparatus according to claim 20, wherein the treatment apparatus is a blood treatment apparatus.

22. The medical treatment apparatus according to claim 21, wherein the blood treatment apparatus is a dialysis system.

23. A medical treatment apparatus for treating at least one fluid, the medical treatment apparatus comprising the blood treatment cassette according to claim 1.

24. The medical treatment apparatus according to claim 23, wherein the treatment apparatus is a blood treatment apparatus.

* * * * *